United States Patent [19]

Chvapil

[11] Patent Number: 4,485,088

[45] Date of Patent: Nov. 27, 1984

[54] METHOD OF TREATMENT OF FIBROTIC LESIONS BY TOPICAL ADMINISTRATION OF LATHYROGENIC DRUGS

[75] Inventor: Milos Chvapil, Tucson, Ariz.

[73] Assignee: Bio-Products, Inc., Tucson, Ariz.

[21] Appl. No.: 362,241

[22] Filed: Mar. 26, 1982

[51] Int. Cl.$^3$ ...................... A61K 9/70; A61K 31/275
[52] U.S. Cl. ........................................ 424/28; 424/304
[58] Field of Search ................................. 424/304, 28

[56] References Cited

PUBLICATIONS

Code of Federal Regulations 37 (7-1-82), p. 38.

Primary Examiner—Stanley J. Friedman

[57] ABSTRACT

The disclosure deals with a method of treating fibrotic lesions related to abnormal collagen polymerization by topical administration of lathyrogenic substances, such as β-aminopropionitrile fumarate, aminoacetonitrile, D-penicillamine, into the site of the injury. The lathyrogenic drugs are administered by local injection or onto the skin and percutaneously transported into the site of the lesion. Lathyrogens, administered locally as a single drug or in combination do not produce any local or systemic toxic effects and are improving the function of the pathological fibrosis based on the accumulation of polymerized collagenous protein.

5 Claims, No Drawings

METHOD OF TREATMENT OF FIBROTIC LESIONS BY TOPICAL ADMINISTRATION OF LATHYROGENIC DRUGS

REFERENCES CITED

E. E. Peacock, Jr. and Walton Van Winkle. *Wound Repair*, Sanders Co. Philadelphia, USA, 1976.

H. Keiser and A. Sjoerdsma. Clin. Pharmacol. Ther. 8: 593, 1967.

E. E. Peacock and J. W. Madden. Surgery 66: 215, 1969.

D. J. Prockop. German Pat. No. 2,228,187 (Dec. 14, 1972).

In human medicine, there has always been an urgent need for an efficient method of inhibiting abnormal accumulation of collagen in the form of fibrotic, cirrhotic or excessive scar lesions. Only in the last decade have various aspects of collagen metabolism and collagen regulating mechanisms made it possible to apply basic knowledge to more integrated and complex systems as represented by various models of fibrosis in animals. The goal of various treatments aiming at the inhibition of collagen metabolism was to inhibit selectively the synthesis and deposition of this fibrous protein specifically in the fibrotic lesion, not in intact tissues. As will be shown below, so far, not an efficient method was developed, in spite of the fact that every aspect of collagen metabolism was taken into such a "therapeutic" consideration. It has been my experience that inhibition of maturation (polymerization, stabilization of the structure) of collagen has so far been the most successful and powerful method of interfering with the physical properties of scar contractures and fibrotic structures. Apparently, it is not the total volume of collagenous structures within a certain tissue, but rather the physical properties of the callogenous matrix which represent the real danger to the function of the tissue or organ. When collagen is cross-linked, possibly by stable covalent cross-links involving the function of lysyl oxidase, it is less degradable by mammalian collagenase and forms a compact rigid scar binding less water. As will be demonstrated below, formation of a scar, which ultimately shrinks, contracts, forms deformities, strictures, represent the real danger for the patient. It is the object of this disclosure to present a new method of topical interference with the formation of mature scars by a group of drugs, called lathyrogens. Lathrogens are defined as a group of chemical substances inhibiting by any method the formation of intermolecular and intramolecular covalent cross-links in collagen or elastin structures.

BACKGROUND INFORMATION

In order to justify my reasons for administering certain drugs called lathyrogens topically into the site of fibrotic lesion, it is necessary to outline several topics related to this new therapeutical method.

Dynamics of Scar Formation

Scar callagen is synthesized by fibroblasts. While still within the fibroblasts, the collagen polypeptides are hydroxylated, form a triple helix and undergo glycosylation to the transport form, known as procollagen. Procollagen is then secreted from the fibroblasts into the extracellular wound environment, to form tropocollagen. Tropocollagen then undergoes intramolecular and intermolecular covalent cross-linking to form collagen fibers which are becoming progressively less soluble and acquiring mechanical strength. This process is also called maturation or polymerization of collagen and is the main target of this invention.

Formation of a scar is the result of a fibroproliferative inflammation. Scar is an imperfect method of repairing tissue defects. Several steps could be identified in the course of fibrotic reaction. The injury activates fibroblasts to produce more collagen and glycosaminoglycans. Often part of the injury is bleeding by ruptured vessels. Blood is a known factor inducing fibrosis. In ruptured or injured tendons, the presence of blood and blood proteins, mainly of fibrin, forms bridges between the tendon and its sheath to form peritendineous adhesions which immobilize the joint by impairing the gliding function of the tendon. Once collagen is formed and accumulates at the site of the injury, it matures and only then do the abnormal functions of the tissue manifest themselves.

In the dynamics of the fibroproductive inflammation, various reactions reach their maximum and then decline with time. Activity of lysyl oxidase, the enzyme which is involved in polymerization of collagen, is highest at much later stages after collagen has been accumulated in the intercellular space. The maximal activity of lysyl oxidase coincides with formation of an insoluble collagen within the injured tissue. Consequently, the optimal time of "pharmacological" interference with a certain step of the inflammation is at the time of maximum incidence and activity of this specific process. We learned by our experiments that in skin incision wounds, the inhibition of lysyl oxidase could be started five days after inflicting the injury, and continued the treatment for 14–21 days to achieve an effective and permanent prevention of collagen maturation.

The fibrotic collagenous tissue is in a continuous increased metabolic turnover. Both synthesis and degradation of collagen are increased and their relative activities change with time of healing. It could be assumed that by decreasing the structural stability in the scar (i.e., decreasing the degree of polymerization of collagen) by administration of lathyrogenic agent, the pool of "extractable" collagen is increased. These forms would be more readily available to digestion by collagenase system and by other proteolytic enzymes in the later stage. This will result in a reduction of the size and volume of the fibrotic mass.

Pharmacology of Fibrosis

There exist several steps unique for collagen which could be used as a target for so-called "specific interference" with collagen metabolism. These stages are:

1. Hydroxylation of prolyl and lysyl residues by appropriate hydroxylases.
2. Glycosylation of some $\epsilon$-NH$_2$ hydroxylysyl groups and;
3. subsequent secretion of the molecule out of the cell.
4. In the extracellular space, the molecule further polymerizes or matures under the effect of lysyl oxidase which forms the basis for development of stable covalent cross-links.
5. At different stages of collagen synthesis the molecule is degradable but the "younger" the molecule is, the faster the degradation by tissue collagenases.

Several sophisticated methods were developed and studied with the aim to reduce collagen deposition or polymerization in the fibrotic lesion (D. J. Prockop German Pat. No. 2,228,187). In all these situations, the medication was administered either perorally or parenterally, in other words by systemic route, where the drug was distributed among all tissue and body fluids.

All various methods of interference with individual steps of collagen synthesis have one major deficiency; they work very nicely in isolated, closed systems of cells in tissue cultures and are minimally effective or quite ineffective in vivo in the whole organism. In fact, after systemic administration of many of these drugs (proline analogs, chelating agents, colchicine, etc.) their toxic effect is close to the therapeutic effect. Thus, there is a permanent risk of general toxicity of the drug used.

The only exception seems to be the use of a lathyrogen to interfere with collagen polymerization mainly because of high effectiveness of a typical representative of lathyrogens, beta-aminopropionitrile (BAPN), to inhibit lysyl oxidase at $10^{-7}$M concentrations. Still, the fast metabolism of BAPN requires frequent administration of this potent drug (every 6 hours seems to be optimal) which may result in induction of some toxic adverse effects in both lab animals as well as in humans.

Maturation (Polymerization of Collagen)

The enzyme forming the basis for the polymerization of collagen is lysyl oxidase. Lysyl oxidase oxidatively deaminates specific ε-amino groups of peptidyl lysine and hydroxylysine residues contained within the structural proteins collagen and elastin. The aldehyde product then forms, nonenzymatically, either Schiff base adducts with other specific ε-amino peptidyl lysine or hydroxylysine residues or forms aldol condensates with other preformed aldehydric components. These cross-linking reactions lend structural integrity to collagenous and elastinous connective tissue.

In principle, we may interfere directly with the function of lysyl oxidase by various lathyrogenic agents, BAPN and aminoacetonitrile being the most effective. Inhibition of lysyl oxidase by BAPN is irreversible. As will be shown below, lysyl oxidase has very high turnover and its activity in a granuloma tissue after a single systemic moderate dose of BAPN recovers within 6–12 hours. Another possibility is blocking the formed aldehydes, as with D-penicillamine, thus preventing condensation of aldehydes or formation of Schiff bases as shown in Scheme I.

Scheme I
Suggested methods of the effect of lathyrogens on the covalent cross-links in the collagen structure.

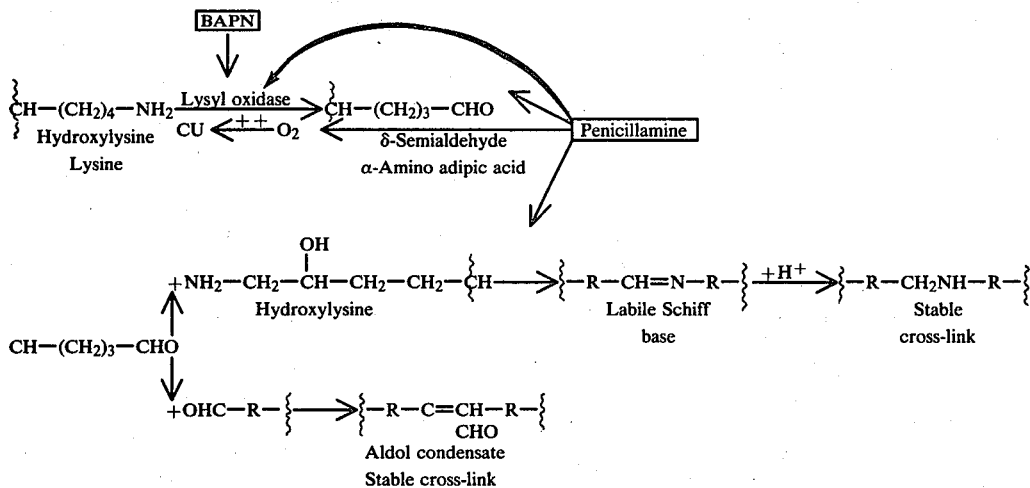

Since BAPN and D-penicillamine affect two different sites in the formation of covalent cross-links, when used together their effect is additive. The lathyritic properties of penicillamine derive from its ability to chelate aldehydes formed by the action of lysyl oxidase on the epsilon amino group of tropocollagen lysine. In addition, direct inhibition of of lysyl oxidase by D-penicillamine was demonstrated. The overall effectiveness of systemically-administered D-penicillamine in decreasing the structural stability of collagen has been well-documented. All of the clinical studies using the treatment with D-penicillamine have indicated a high incidence of acute hypersensitivity reactions. Striking changes in the metal content in various tissues and fluids after D-penicillamine treatment were reported. It is mainly the metabolism of zinc and copper which is affected and which results in various deficiencies and pathologies. These symptoms are suppressed by systemic steroids; thus, a combination of D-penicillamine and prednisone should minimize toxic side effects. Topical administration of D-penicillamine by injection route or by percutaneous absorption similar to BAPN uses several times lower dose than that used systemically. This avoids the incidence of toxic complications.

Toxicity of Systemically-Administered Lathyrogens

The systemic toxicity of BAPN has been the major obstacle in using this drug in large scale in human pathology. There is no doubt that at lathyrogenic dosages of BAPN, the animals stop growing, lose body weight and lower their food intake. Also, the animal's behavior is changed—they do not clean their fur and are irritated if they are touched. All this indicates a general toxicity. There is also no doubt that various lathyrogenic drugs, mainly BAPN showed to be very effective in the blocking the polymerization of collagen in various animal models of fibrotic lesion.

Because of success in animal studies, Keiser and Sjoerdsma (1967) studied the effect of BAPN in patients with fibrotic lesions of the skin and other organs called scleroderma. In short-term treatment with a dose of 2 g/day, no toxic side effects were noted; longer courses of treatment were, however, associated with prohibitive reactions, such as allergic skin rash and hemolytic anemia. Peacock and Madden (1969) employed BAPN in clinical trials with humans undergoing flexor tendon surgery. Although a significant number of the patients exhibited hypersensitivity to the agent, decreased covalent bonding of human collagen with significant clinical benefit was demonstrated.

One way to reduce the systemic toxicity of BAPN without interfering with its lathyrogenic activity is to inhibit the metabolism of this drug. If degradation of BAPN is blocked by pargyline, a monoamine oxidase (MAO) inhibitor, prolonged lysyl oxidase inhibition potentiates wound strength diminution without accompanying toxicity. Indeed, isoniazid (INH), both a weak lysyl oxidase and MAO inhibitor potentiate the lathyritic effects of BAPN. The addition of isoniazid or pargyline to an otherwise effective dose of BAPN profoundly inhibited lysyl oxidase and depressed wound burst strength. All animals gained weight throughout the experiment.

In order to overcome the general toxicity of systemically administered BAPN, I studied two methods, both of which showed to be unsuccessful. In the first method BAPN was bound by amide- and ionic linkage to a polymer such as polyacrylic acid, with the aim to obtain long lasting sustained release of the drug. It was found, however, that many carriers for BAPN induced nonacceptable fibrotic tissue reaction when injected in injured tissues. The second approach intended to increase the percutaneous absorption of BAPN by synthesizing BAPN base. Indeed it was demonstrated that BAPN base penetrates the skin barrier approximately five times faster than BAPN fumarate. Unfortunately, the base showed to be unstable under storage, undergoing hydrolysis forming ammonia and toxic acrylonitrile. For these reasons we discontinued the use of either polymer-BAPN fumarate complex of BAPN-base.

Based on the evidence of systemic toxicity of BAPN, I arrived at the conclusion that the only method of preventing the toxic problems of this clinically important and needed drug is to administer BAPN and other lathyrogens topically. There exist several clinical symptoms with collagen pathology, which could be treated with benefit by topically administered BAPN. These include skin scar contractures, such as after deep burns, peritendineous adhesions after injury to the tendon, perineural adhesions, stiffness of periarticular tissue of immobilized joints and Dupuytren's contracture and other fibrotic lesions common in human and veterinary medicine.

Although the pathogenesis of the above disorders may differ, in every one it was postulated that the physical properties of the scar tissue were affected by abnormal cross-linking of the collagenous component. A variety of methods was proposed and used to alleviate the problems of abnormal reactivity of polymerized scar tissue (Peacock and Van Winkle 1976). In all the above manifestations BAPN systemic administration was suggested. The ideal method of topical administration would be the noninvasive percutaneous resorption of BAPN painted onto the skin as proposed in this disclosure. I will show that BAPN is transported through the skin and effectively inhibits lysyl oxidase in granuloma tissue formed in subcutaneously implanted polyvinyl alcohol sponge. At the same time, no morphological or ultrastructural evidence of topical cytotoxicity is found. These findings assured me that topical BAPN is safe, effective and optimal therapeutic regimen to achieve significant interference with maturation of collagenous structure in tissues with an injury.

Peritendineous adhesions as well as stiffness is injured or immobilized joints is a major clinical problem. Complete rehabilitation of a patient may be prolonged or prevented by such adhesions, scar contractures or joint stiffness. The lesions are due to the formation and remodeling of collagen within scar, ligaments, or fascia. It was shown experimentally in rats and dogs that inhibition of collagen cross-linking in and around tenolyzed tissue or an immobilized joint using systemically-administered BAPN could significantly improve the tendon gliding fraction or reduce stiffness. In both species, however, the systemic administration of the lathyrogen resulted in undesirable side effects. Still, the beneficial effects on reducing adhesions or joint stiffness have encouraged my efforts to introduce the lathyrogen locally at the site of the tendon lesion or over the immobilized joint by topical administration.

Percutaneous Resorption

This disclosure proposes to inhibit collagen in specific fibrosis related lesions either by topical application of BAPN or other lathyrogens onto the skin or by direct injection into the lesion. The major limitation of topical drug administration onto the skin surface is the imposing impermeability of the skin, which forms a chemical and waterproofing seal. By several studies it was shown that the rate of percutaneous resorption is limited mainly by the stratum corneum, formed by 15 cells thick layer of cornified cells. Substantial knowledge has been accumulated and reviewed on the permeability of the skin.

It was shown that the rate of transport of some solutes through the skin depends on:

(a) polar-nonpolar nature of the substance
(b) hydration of the skin
(c) blood supply
(d) modification of the stratum corneum by chemicals.

Accordingly, non-charged molecules penetrate faster. I demonstrated this by showing higher penetration of BAPN-base than that of BAPN-fumarate. The instability of the base is, however, the major obstacle in using this drug. Occlusive bandage with the solutes enhances penetration considerably. UV-irradiation of the skin, causing erythema, is supporting percutaneous resorption. Detergents, dimethylsulfoxide (DMSO) and several other solvents have been shown to substantially increase the process. Beta-aminopropionitrile (BAPN), as the term is used herein, includes both free BAPN and BAPN salts, such as BAPN-fumerate, which also function to inhibit lysyl oxidase. The various solvents and solvent mixtures, including aqueous buffers, and water-containing solvent systems, such as buffer/DMSO, which are used to carry BAPN for topical administration are also referred to herein as drug carriers. It will be understood by those skilled in the art that such carries may be formulated to contain emulsifiers or the like for use particularly in compounding the BAPN for external topical, i.e., percutaneous administration. The drug and its drug carrier are referred to, collectively, as a drug preparation.

This disclosure will demonstrate that BAPN-fumarate effectively penetrates the stratum corneum barrier, and is excreted into urine, if administered onto the pretreated skin by a method described by this invention. The most important is, however, that due to this transport, BAPN inhibits collagen maturation (lysyl oxidase activity) in the subcutaneously induced granuloma tissue. This makes it possible to use the simplest method of BAPN administration, i.e., painting the pretreated skin with BAPN base fluid in combination with occlusive dressing or to use special delivery system as consisting of hydrophilic pouch containing the solution of the drug described in this disclosure.

OBJECTIVES OF THIS INVENTION

It is the object of this invention to demonstrate that topically administered substances delivered locally to the site of the fibrotic injury and interfering with collagen polymerization and called lathyrogens are not causing any side toxic effects local or systemic.

Another object of this invention is to show that topically administered lathyrogens are effectively changing the functional characteristics of the fibrotic lesions.

Yet another object of this invention is to show that a lathyrogen such as $\beta$-aminopropionitrile (BAPN) when administered topically on the skin adjacent to the underlying fibrotic lesion, is penetrating across the skin by a process called percutaneous absorption and is affecting the chemistry and function of the fibrotic injury.

Yet another object of this invention is to show that direct injection of lathyrogens into the lesion such as injury to the tendon called tendinitis or tendovaginitis is effectively improving the clinical picture of the disease.

Finally, the invention will demonstrate that combination of lathyrogens such as $\beta$-aminopropionitrile and D-penicillamine administered topically into the lesion by injection or applied onto the intact skin by method of percutaneous absorption allowing both drugs to penetrate into the fibrotic lesion is more effective than the administration of either substance alone.

The invention is further and more specifically explained by the following examples which are given by way of illustration and not by way of limitation.

EXAMPLE 1 will demonstrate that a solution of a lathyrogen applied onto the skin penetrates the skin barrier and is detectable in the urine.

Adult rats, Sprague Dawley strain, were shaved on the dorsum. A 0.1 ml solution of 0.16M $\beta$-aminopropionitrile fumarate, containing 30 mg BAPN/ml of phosphate buffer (0.1M, pH 7.2) and for easy detection 2 $\mu$Ci of $^{14}$C-$\beta$-aminopropionitrile fumarate was painted on the shaved skin area 2×2 cm of a rat. In another rat, the shaved skin was washed first with 2% Ivory soap, in the next group the skin area after painting was covered with occlusive bandage. In another group of rats (Table 1) the drug was administered onto the skin the drug in 60% dimethyl sulfoxide, a solvent known to increase percutaneous absorption. Finally, in the last group (Table 1), the basic solution was administered into a small container made of a hydrogel polymer. This hydrogel is characterized by containing 80% water. It makes good contact with the skin, allows penetration of the drug through the container wall, hydrates the skin under the occlusive dressing, thus enhancing the percutaneous transport.

TABLE 1

EFFECT OF VEHICLE AND SKIN PRETREATMENT ON THE PERCUTANEOUS ABSORPTION OF BAPN-FUMARATE IN THE RAT

| Group | Drug Recovery in the Urine % Recovered in 6 hours |
|---|---|
| 1. BAPN-F in phosphate buffer on intact skin | 0.97 |
| 2. BAPN-F in phosphate buffer skin washed with 2% Ivory soap | 2.17 |
| 3. BAPN-F in phosphate buffer skin washed with 2% Ivory soap, occlusive bandage | 10.56 |
| 4. BAPN-F in phosphate buffer in 60% DMSO | 11.66 |
| 5. BAPN-F in phosphate buffer in 60% DMSO skin washed in 2% Ivory soap | 10.10 |
| 6. BAPN-F* in phosphate buffer skin washed with 2% Ivory soap applied in hydrophilic container, occlusive bandage | 35.00 |

$^{14}$C—BAPN-fumarate, 2 $\mu$Ci in 30 mg BAPN-fumarate/ml, 0.1 ml applied/skin area
DMSO is dimethyl sulfoxide
*% recovered in 24 hours The results, shown in Table 1 indicate the importance of cleaning the skin from contaminating lipids and keratinous debris by Ivory soap (Group 2). It also shows the significant role of occlusive dressing on the magnitude of percutaneous transport (Group 3). The enhancement by DMSO is documented by the results of Groups 4 and 5. The major accomplishment was the continuous delivery of the drug through a hydrophilic container, attached to the skin by occlusive dressing formed by surgical tape Blenderm (3M Company, Minnesota). By this method (Group 6) the delivery was increased almost 40 times when compared with Group 1. It is obvious that by this container a sustained release of the lathyrogen or combination of this drug could be obtained and that its (their) penetration across the skin barrier is achieved.

EXAMPLE 2 shows a method of delivering the lathyrogen across the skin barrier by sustained release from a bag made of a hydrogel polymer.

The experimental conditions were similar to those of Example 1 for Group 6. A 0.4 ml solution of 1.1M $\beta$-aminopropionitrile fumarate containing 200 mg/ml and 2 $\mu$Ci of the same $^{14}$C labeled substance was placed into a hydrophilic bag membrane. This membrane contained 80% water. The container bag was placed onto the shaved skin area of 4 cm$^2$, covered with impermeable occlusive dressing represented by Blenderm surgical tape (3M, Minnesota). The rats were placed in metabolic cages and at defined time intervals, the urine was collected and the amount of radioactive drug determined. Table 2 shows that during 120 hours of observation 22.5% of the drug penetrated across the skin and that the release was continuous at the constant rate.

TABLE 2

RECOVERY OF β-AMINOPROPIONITRILE FROM THE URINE AFTER ITS ADMINISTRATION ON THE SKIN OF RATS THROUGH A HYDROPHILIC BAG CONTAINER

| Time (hours) | Recovery in Urine (In % of the Total Dose) |
|---|---|
| 4 | 0.5 |
| 8 | 1.01 |
| 12 | 2.37 |
| 24 | 5.40 |
| 72 | 9.9 |
| 96 | 15.2 |
| 120 | 22.5 |

Time indicates the urine sampling period. Recovery is given in percent of the dose administered into the hydrophilic bag.

EXAMPLE 3 shows that a lethal dose of a lathyrogen administered percutaneously is almost ten times higher than when administered systemically by intraperitoneal injection.

The determination of lethal dose, killing within a certain time after the administration of the tested drug 50% of the exposed animals, is a standard method of evaluation of the toxicity of a drug.

A total of 40 male CD-1 mice with a body weight of 20 g were injected either intraperitoneally with β-aminopropionitrile fumarate or the drug was applied in a solution onto the shaved dorsal aspect of the skin. Four dosage levels spaced in geometric progression were evaluated using five animals for each dose. After administration, the animals were observed for a 24-hour period for incidence of death. The results shown in Table 3 demonstrate that $LD_{50}$ for intraperitoneally administered BAPN-fumarate is at least 10 times higher than when the drug is given percutaneously.

TABLE 3

ACUTE TOXICITY OF β-AMINOPROPIONITRILE FUMARATE ADMINISTERED INTRAPERITONEALLY OR TOPICALLY ON THE SKIN

| | $LD_{50}$ (g/kg body weight) | |
|---|---|---|
| | intraperitoneally | percutaneously |
| BAPN-fumarate | 3.0 | 23.1 |

EXAMPLE 4 demonstrates the effectiveness of the drug, β-aminopropionitrile fumarate, in the fibrotic lesion in the subcutis after application of onto the intact skin.

Two groups of rats, four rats in each group, 250 g body weight, Sprague-Dawley males, were implanted subcutaneously with a polyvinylalcohol sponge (Ivalon, Unipoint Labs, New Jersey) in the dorsal region through an incision distal from the placement of the sponge.

A solution of 0.1 ml of β-aminopropionitrile (200 mg BAPN/ml) was applied every 12 hours onto the skin over the implanted sponge for a total of seven days. Then the rats were sacrificed, reactive granuloma tissue excised and used for the determination of the activity of lysyl oxidase.

The results in Table 4 show significant inhibition of the enzyme activity in the lesion when BAPN was painted over the implanted sponge. This documents that the drug penetrates across the skin barrier into the site of the fibrotic injury and exerts its inhibitory effect on the enzyme involved in the polymerization of collagen structures.

TABLE 4

EFFECT OF TOPICAL APPLICATION OF β-AMINOPROPIONITRILE FUMARATE ON THE ACTIVITY OF LYSYL OXIDASE IN THE GRANULOMA TISSUE OF RATS

| Group | Lysyl Oxidase Activity DPM/mg protein |
|---|---|
| Control (no treatment) | 36.2 ± 7.1 |
| | $P < 0.001$ |
| BAPN-fumarate, topical | 1.8 ± 0.3 |

There were four rats in each group.
Variability is given by standard deviation.
Significance of the results tested by Student's t-test.

EXAMPLE 5 will document the therapeutic effectiveness of direct infusions of β-aminopropionitrile fumarate solution into the dissected peritendinous adhesions in a rooster model of tendon injury.

Adult White Leghorn chickens were sedated with Pentothal, fixed to the operating table and given metacarpal local anesthesia with 1% xylocaine. Following surgical prep of the foot, a tourniquet was applied. Through a mid-lateral incision the sublimus tendon was removed from the long digit of both feet and a 4-0 braided stainless steel wire was passed through the entire length of the remaining profundus tendon to promote injury to the tendon by "scarification". The incision was closed with a continuous nylon suture, 4-0. Both feet were then incorporated in a plaster of Paris dressing with the feet in a functional position permitting the animals to walk while in the plaster.

Three weeks later the animals were prepared for surgery as above and the original incision was opened. A complete tenolysis was performed freeing the profundus tendon from surrounding fibrotic adhesions. The wound was closed using a continuous 4-0 nylon suture. A 1.0 ml silastic tube was prepared with multiple perforations over 3.0 centimeters of its distal end. This tube was placed along side the digit operated upon and the digit with tube incorporated in a "Saran-Wrap" sheath. The foot was again incorporated in a walking plaster in a functional position with the silastic tube emerging from the proximal end of the cast. A Leur lock was attached to the tube permitting the infusion of 0.3 l of 1.6M beta-aminopropionitrile fumarate (300 mg/ml) every 12 hours for 5 days. Controls received 0.3 ml of saline.

After 5 days of BAPN application the animals were sacrificed, the plaster dressings removed, and the legs amputated. The flexor profundus tendon to the digit which had undergone tenolysis was isolated at the level of the "ankle" and a traction wire was placed using a Bunnel suturing technique. The leg was then mounted in an Instron Tensiometer and measured traction was applied to the flexor profundus tendon at a rate of 2.5 cm/min while the flexion of the three digital joints was measured. Data permitted the calculation of "Work of Flexion" which is defined as the tension force required to flex the digit (toe-tip to the sole) divided by the sum of the degrees of flexion of the three joints of the digit.

TABLE 5

| TOPICAL BAPN-FUMARATE | | |
|---|---|---|
| | Application | Control (Saline) |
| Work of Flexion (Mean) | 13.10 gm/degree | 44.8 gm/degree |
| Standard Deviation | 4.25 | 9.9 | t-statistic (paired data) = −3.94
$P < 0.01$

Table 5 shows that tendons treated with topical BAPN-fumarate glided more easily; much lower force was needed to flex the finger. Similar results were obtained by direct injection of BAPN-fumarate solution into the injured tendon.

DESCRIPTION OF THE INVENTION

The invention deals with a treatment of pathological situations arising from accumulated collagenous tissue in the form of a scar, fibrotic adhesions or increased formation of stable crosslinks in the collagenous matrix by local administration of lathyrogenic substances, such as β-aminopropionitrile or D-penicillamine either onto the skin or by local injection of the sterile solution of the above drugs or their combination into the site of the lesion. In the first case, solution of β-aminopropionitrile, containing 100 mg to 300 mg per milliliter of water is painted at 12 hour intervals onto the soap washed skin. It is possible to apply the drug to the skin over the lesion at the same concentrations in the carrier of a gel, ointment, jelly for easier administration. The treatment should be administered for a period of 2 to 12 weeks, depending on the nature of the fibrotic pathology. It is with advantage to wash the skin first with a keratolytic agent such as 20% solution of salicylic acid or 20% solution of urea to increase the percutaneous transport of the drug or combination of both drugs. It is also with advantage to cover the site of treatment with an occlusive dressing consisting of impermeable polymer adhesive tape.

The other method of topical administration of lathyrogens consists of the direct injection of sterile solution of 2-5mM β-aminopropionitrile with a 26 gauge needle into the lesion. Approximately 0.4 ml of the solution is injected at one site, number of injection sites depend on the type and size of the pathology. In general, the injections are placed 2 cm apart, thus infiltrating the lesion. The injections are repeated daily for a period of 1-6 weeks, depending on the type of the pathology. In the case D-penicillamine is used, the concentration of this drug for local injections is 10-30mM. Same volume per injection site and frequency of the injection is used with D-penicillamine as with β-aminopropionitrile.

It is with advantage to use the combination of both drugs either for percutaneous application or for local injections.

The effective therapeutic dose of D-penicillamine in either application method is always 2-6 times higher than that of β-aminopropionitrile dose.

What is claimed is:

1. A method of treating a wound to reduce the extent of collagen crosslinking at the wound site, comprising
   preparing a drug preparation containing beta-aminopropionitrile in a drug carrier, and
   applying a therapeutically effective amount of the drug preparation locally to the wound site.

2. The method of claim 1, wherein the drug preparation is prepared to include beta-aminopropionitrile at a concentration between about 0.2M and 2M, and said applying includes placing the preparation in contact with the skin surface of the wound site.

3. The method of claim 2, wherein the drug carrier includes water or water and DMSO, and said applying includes placing the drug preparation on the skin at the wound site, and covering the site with an occlusive material to reduce drying at the site.

4. The method of claim 3, wherein the drug preparation is contained in a porous hydrophilic support which is placed against the skin surface of the wound site.

5. The method of claim 2, wherein said applying includes infusing the wound site subcutaneously with the drug preparation.

* * * * *